United States Patent
Rapoport (10) Patent No.: US 8,847,608 B2
(45) Date of Patent: Sep. 30, 2014

(54) SYSTEM AND METHOD FOR A NONDESTRUCTIVE ON-LINE TESTING OF SAMPLES

(76) Inventor: Uri Rapoport, Moshav Ben Shemen (IL)

(*) Notice: Subject to any disclaimer, the term of this patent is extended or adjusted under 35 U.S.C. 154(b) by 494 days.

(21) Appl. No.: 13/234,433

(22) Filed: Sep. 16, 2011

(65) Prior Publication Data

US 2012/0038371 A1   Feb. 16, 2012

Related U.S. Application Data

(63) Continuation-in-part of application No. 12/377,980, filed as application No. PCT/IL2007/001043 on Aug. 21, 2007, now abandoned.

(60) Provisional application No. 60/838,887, filed on Aug. 21, 2006.

(51) Int. Cl.
 *G01R 27/04* (2006.01)
 *G01N 24/08* (2006.01)

(52) U.S. Cl.
 CPC .................... *G01N 24/085* (2013.01)
 USPC ................ 324/633; 324/71.1; 324/309

(58) Field of Classification Search
 USPC .................. 324/309, 322, 663, 71.1
 See application file for complete search history.

(56) References Cited

U.S. PATENT DOCUMENTS

| 2005/0116712 A1* | 6/2005 | Corver et al. ............. 324/309 |
| 2008/0111549 A1* | 5/2008 | Nabetani ................. 324/322 |

* cited by examiner

*Primary Examiner* — Vincent Q Nguyen
(74) *Attorney, Agent, or Firm* — The Law Office of Michael E. Kondoudis (57) ABSTRACT

A non-destructive on-line system for detecting a presence of a material in a sample of a substance, including: an MRI device; a flow conduit encompassed by the tunable RF coil of the MRI device and having an input duct and an output duct; a flow of the sample through the flow conduit; a signal detector for detecting frequency-dependent output signals from the MRI device as a function of a frequency variation of the RF tunable coil within a frequency range of an RF resonant frequency of a standard sample of the substance, and a processing unit.

14 Claims, 7 Drawing Sheets

SYSTEM AND METHOD FOR A NONDESTRUCTIVE ON-LINE TESTING OF SAMPLES

FIELD OF THE INVENTION

The present invention relates to systems and a method for nondestructive on-line testing of a sample of a substance by means of an MRI device generating RF frequency-dependent MRI signals. The MRI signals are processed and analyzed to optimize and improve the production process of the substance.

BACKGROUND OF THE INVENTION

The following prior art is believed to be the current status of the art:

U.S. Pat. No. 6,401,519 describes an improved system for measuring off-line characteristics of fluids.

Chinese Patent No. 1,417,588 describes an on-line water quality monitoring network system including an on-line monitoring instrument comprising physical parameter sensor, chemical pollutant density analyzer and in-situ flow meter.

U.S. Pat. No. 5,522,988 describes an on-line coupled liquid and gas chromatography system with an interface capillary tube interposed between a pair of capillary chromatographic columns.

EP 0730 164 A1 describes an MRI apparatus and method for nondestructive quality assessment and analysis of a sample, such as an unmilled rice grain and a unhulled rice seed. The sproutability of the rice seed and rice grain are determined from the MRI analysis of the food products.

The prior art references do not describe systems and/or methods for optimizing and improving industrial production processes, for industries such as the food production industry, by on-line nondestructive systems and methods.

Thus, there is an unmet need for on-line nondestructive systems and methods for controlling industrial production processes.

SUMMARY OF THE INVENTION

The present invention relates to systems and a method for on-line nondestructive monitoring of a sample of a substance by introducing the sample into an MRI device and generating RF frequency-dependent MRI signals within a frequency range of the resonant frequency of the substance. The generated MRI signals are processed and analyzed to optimize and improve the production process of the substance by determining therefrom, reactances and inductances of samples of substances.

In the present invention, the RF frequency of the tunable RF coil of the MRI device generates MRI RF signals which are detected and processed, as known in the art. By means of Smith Curve software codes, the frequency-dependent reactances and inductances of samples of substances are determined. Frequency difference curves are generated and the amount of water, for example, found in the sample is determined.

Thus, using the present invention in a food production industry, it is possible to determine the quality of the substance undergoing examination, for example, by determining the relative amount of water contained in the sample. It is known in the art, that an MRI signal generated by a substance is dependent on the number of protons in the sample. Therefore, the MRI signal is dependent on the amount of water contained in the sample of the substance. Thus, a sample which includes an amount of water which is greater than a standard sample of the substance, generates a larger MRI RF signal than that which is generated by a standard sample. This is beneficial to the food industry.

Using the present invention it is possible to check the contents of a sample of a substance, such as an amount of water in a food product, by using an MRI device and the relevant peripheral devices, as described hereinbelow. Therefore, using the present invention it is possible to ascertain and check if a food product, for example, fulfills the statutory contents' requirements.

In addition, the present invention is configured for optimizing a production process of a substance by ensuring that the production process fulfills requisite requirements. For example, in the food industry, it is possible to check additional contents of the food products, such an acidity parameter in the food product as well as the amount of water contained in the food.

Furthermore, the present invention is adapted to measure and control water pollution by examining the MRI signals from water contaminant, such as an organic contaminant and/or an inorganic contaminant.

In the present invention, the sample to be tested is in a fluid state or in a solid state.

The non-destructive on-line system of the present invention is also adaptable for detecting a presence of at least one material and a characteristic of the material, such as the size of microns (e.g., 0.1 to 10 mm, 10-100 mm, 100 to 1,500 mm), millimeters and centimeters, predefined size distribution and particles shape, $A_W$ water content and any combination thereof.

The present invention is also adapted to determine properties of substances, such as: physical parameters, such as the boiling point, refractive index, viscosity, moisture content, rheologic properties and magnetic properties, electrochemical parameters, such as conductivity, pH, oxygen content, permittivity permeability and dielectric constant, chemical properties, such as chemical concentration and identity of the composition and any combination thereof and biological properties, such as bacteria, mold, fungi, alga, virus, microorganisms, eukaryotes and any combination thereof.

It is one object of the invention to disclose a non-destructive on-line system for detecting a presence of a material in a sample of a substance comprising: an MRI device; a flow conduit encompassed by the tunable RF coil of said MRI device and having an input duct and an output duct; a flow of said sample through said flow conduit; a signal detector for detecting frequency-dependent output signals from said MRI device as a function of a frequency variation of the RF tunable coil within a frequency range of an RF resonant frequency of a standard sample of said substance, and a processing unit, wherein said processing unit is configured to: determine an impedance frequency variation from said frequency-dependent output signals and at least one MRI device operational parameter; determine an RF frequency variation of at least one characteristic parameter of said substance from said impedance frequency variation, and compare said RF frequency variation of said at least one characteristic parameter of said sample with an RF frequency variation of a corresponding characteristic of a standard sample of said substance such that said comparison determines said material content of said sample.

It is one object of the invention to disclose the non-destructive on-line system as defined above, wherein said at least one characteristic of said substance is selected from the group consisting of at least one physical characteristic, at least one electrochemical characteristic, at least one chemical characteristic and at least one biological (PPECB) characteristic and any combination thereof.

It is another object of the invention to disclose the non-destructive on-line system as defined above, wherein said at least one characteristic comprises an electrical inductance of said substance.

It is another object of the invention to disclose the non-destructive on-line system as defined above, wherein said at least one characteristic comprises an electrical reactance of said substance.

It is another object of the invention to disclose the non-destructive on-line system as defined above, wherein said frequency range is approximately ±100 MHz of said resonant frequency.

It is another object of the invention to disclose the non-destructive on-line system as defined above, wherein said material comprises water.

It is another object of the invention to disclose the non-destructive on-line system as defined above, wherein said output signal comprises a voltage signal.

It is another object of the invention to disclose the non-destructive on-line system as defined above, wherein said voltage signal comprises an RF voltage signal.

It is another object of the invention to disclose the non-destructive on-line system as defined above, wherein said processing unit is further configured to optimize a production process of said sample.

It is another object of the invention to disclose the non-destructive on-line system as defined above, wherein adapted to measure and control the sample undergoing a modification said modification is selected from the group consisting of a physical modification, biological modification, chemical modification and any combination thereof.

It is another object of the invention to disclose the non-destructive on-line system as defined above, wherein said sample is selected from the group consisting of tomato puree, tomato ketchup, tomato paste, tomato sauce, tomato beverage, tomato soup, tomato concentrate, apple puree, apple paste, apple sauce, apple beverage, apple concentrate, potato puree, potato paste, potato sauce, potato beverage, potato concentrate.

It is another object of the invention to disclose the non-destructive on-line system as defined above, wherein the system adapted to measure and to control water pollution by at least one contaminant said at least one contaminant is selected from organic contaminants, inorganic contaminants and any combination thereof.

It is another object of the invention to disclose the non-destructive on-line system as defined above, wherein the system adapted to measure an acidity parameter in a food product.

It is another object of the invention to disclose the non-destructive on-line system as defined above, wherein said physical parameter is selected from the group consisting of boiling point, refractive index, viscosity, moisture content, rheologic properties, magnetic properties.

It is another object of the invention to disclose the non-destructive on-line system as defined above, wherein electrochemical parameter is selected from conductivity, pH, oxygen content, permittivity permeability, dielectric constant and any combination thereof.

It is another object of the invention to disclose the non-destructive on-line system as defined above, wherein said chemical parameter is selected from the group consisting of chemical concentration and identity of the composition and any combination thereof.

It is another object of the invention to disclose the non-destructive on-line system as defined above, wherein said biological parameter is selected from the group consisting of bacteria, mold, fungi, alga, virus, microorganisms, eukaryotes and any combination thereof.

It is another object of the invention to disclose the non-destructive on-line system as defined above, wherein said sample is further selected from the group consisting of a solid, a sol-gel, a super-critical solution and any combination thereof.

It is another object of the invention to disclose the non-destructive on-line system as defined above, wherein said material is further selected from the group consisting of water-miscible fluids, water-immiscible fluids, aggregated solutions, dispersions, emulsions, solution, slurry, polymer, solid and powder and any combination thereof.

It is another object of the invention to disclose the non-destructive on-line system as defined above, wherein said solid is selected from the group consisting of nano-particles, fine powders, flowing solids and any combination thereof.

It is another object of the invention to disclose the non-destructive on-line system as defined above, wherein said processor provides a Smith Chart of said impedance frequency variation as a function of said RF frequency such that said impedance frequency variation is function of the reactance and inductance of fluid sample.

It is another object of the invention to disclose the non-destructive on-line system as defined above, wherein said sample comprises a fluid state.

It is another object of the invention to disclose the non-destructive on-line system as defined above, wherein said sample comprises a solid state.

It is another object of the invention to disclose a method for detecting a material in a sample of a substance comprising: providing an MRI device; providing a flow conduit encompassed by the tunable RF coil of said MRI device; providing a flow of said sample through said flow conduit; detecting frequency-dependent output signals from said MRI device as a function of a frequency variation of the RF tunable coil within a frequency range of an RF resonant frequency of a standard sample of said substance, and determining an impedance frequency variation from said frequency-dependent output signals and at least one predetermined MRI operational parameter; determining an RF frequency variation of at least one characteristic of said substance from said impedance frequency variation; comparing said RF frequency variation of said at least characteristic of said substance with an RF frequency variation of a corresponding characteristic of a standard sample of said substance, wherein said comparison determines said material content of said sample.

It is another object of the invention to disclose method as defined above, wherein said at least one characteristic of said substance is selected from the group consisting of at least one physical characteristic, at least one electrochemical characteristic, at least chemical characteristic and at least one biological (PPECB) characteristic and any combination thereof.

It is another object of the invention to disclose method as defined above, wherein said at least one characteristic comprises an electrical inductance of said substance.

It is another object of the invention to disclose method as defined above, wherein said at least one characteristic comprises an electrical reactance of said substance.

It is another object of the invention to disclose method as defined above, wherein said frequency range is approximately ±100 MHz of said resonant frequency.

It is another object of the invention to disclose method as defined above, wherein said material comprises water.

It is another object of the invention to disclose method as defined above, wherein said output signal comprises a voltage signal.

It is another object of the invention to disclose method as defined above, wherein said voltage signal comprises an RF voltage signal.

It is another object of the invention to disclose method as defined above, wherein the method further comprising optimizing a production process of said sample.

It is another object of the invention to disclose method as defined above, wherein the method further comprising measuring and controlling said sample undergoing a modification said modification is selected from the group consisting of a physical modification, biological modification, chemical modification and any combination thereof.

It is another object of the invention to disclose method as defined above, wherein said sample is selected from the group consisting of tomato puree, tomato ketchup, tomato paste, tomato sauce, tomato beverage, tomato soup, tomato concentrate, apple puree, apple paste, apple sauce, apple beverage, apple concentrate, potato puree, potato paste, potato sauce, potato beverage, potato concentrate.

It is another object of the invention to disclose method as defined above, wherein the method further comprising measuring and controlling water pollution by at least one contaminant said at least one contaminant is selected from organic contaminants, inorganic contaminants and any combination thereof.

It is another object of the invention to disclose method as defined above, wherein the method comprising measuring an acidity parameter in a food product.

It is another object of the invention to disclose method as defined above, wherein said physical parameter is selected from the group consisting of boiling point, refractive index, viscosity, moisture content, rheologic properties, magnetic properties.

It is another object of the invention to disclose method as defined above, wherein said electrochemical parameter is selected from conductivity, pH, oxygen content, permittivity permeability, dielectric constant and any combination thereof.

It is another object of the invention to disclose method as defined above, wherein said chemical parameter is selected from the group consisting of chemical concentration and identity of the composition and any combination thereof.

It is another object of the invention to disclose method as defined above, wherein said biological parameter is selected from the group consisting of bacteria, mold, fungi, alga, virus, microorganisms, eukaryotes and any combination thereof.

It is another object of the invention to disclose method as defined above, wherein said sample is further selected from the group consisting of a solid, a sol-gel, a super-critical solution and any combination thereof.

It is another object of the invention to disclose method as defined above, wherein said material is selected from the group consisting of water-miscible fluids, water-immiscible fluids, aggregated solutions, dispersions, emulsions, solution, slurry, polymer, solid and powder and any combination thereof.

It is another object of the invention to disclose method as defined above, wherein said solid is selected from the group consisting of nano-particles, fine powders, flowing solids and any combination thereof.

It is another object of the invention to disclose method as defined above, wherein said method further comprising providing a Smith Chart of said impedance frequency variation as a function of said RF frequency such that said impedance frequency variation is function of the reactance and inductance of fluid sample.

It is another object of the invention to disclose method as defined above, wherein said sample comprises a fluid state.

It is another object of the invention to disclose method as defined above, wherein said sample comprises a solid state.

It is another object of the invention to disclose a non-destructive on-line system for detecting a presence of a material in a sample of a substance comprising: an MRI device; a container encompassed by the tunable RF coil of said MRI device containing said sample; a signal detector for detecting frequency-dependent output signals from said MRI device as a function of a frequency variation of the RF tunable coil within a frequency range of an RF resonant frequency of a standard sample of said substance, and a processing unit, wherein said processing unit is configured to: determine an impedance frequency variation from said frequency-dependent output signals and at least one MRI device operational parameter; determine an RF frequency variation of at least one characteristic parameter of said substance from said impedance frequency variation, and compare said RF frequency variation of said at least one characteristic parameter of said sample with an RF frequency variation of a corresponding characteristic of a standard sample of said substance such that said comparison determines said material content of said sample.

It is another object of the invention to disclose the system as defined above, wherein said at least one characteristic of said substance is selected from the group consisting of at least one physical characteristic, at least one electrochemical characteristic, at least one chemical characteristic and at least one biological (PPECB) characteristic and any combination thereof.

It is another object of the invention to disclose the system as defined above, wherein said at least one characteristic comprises an electrical inductance of said substance.

It is another object of the invention to disclose the system as defined above, wherein said at least one characteristic comprises an electrical reactance of said substance.

It is another object of the invention to disclose the system as defined above, wherein said frequency range is approximately ±100 MHz of said resonant frequency.

It is another object of the invention to disclose the system as defined above, wherein said material comprises water.

It is another object of the invention to disclose the system as defined above, wherein said output signal comprises a voltage signal.

It is another object of the invention to disclose the system as defined above, wherein said voltage signal comprises an RF voltage signal.

It is another object of the invention to disclose the system as defined above, wherein said processing unit is further configured to optimize a production process of said substance.

It is another object of the invention to disclose the system as defined above, wherein the system is adapted to measure and control a sample undergoing a modification said modification is selected from the group consisting of a physical modification, biological modification, chemical modification and any combination thereof.

It is another object of the invention to disclose the system as defined above, wherein said sample is selected from the group consisting of tomato puree, tomato ketchup, tomato paste, tomato sauce, tomato beverage, tomato soup, tomato concentrate, apple puree, apple paste, apple sauce, apple beverage, apple concentrate, potato puree, potato paste, potato sauce, potato beverage, potato concentrate.

It is another object of the invention to disclose the system as defined above, wherein the system adapted to measure and to control water pollution by at least one contaminant said at least one contaminant is selected from organic contaminants, inorganic contaminants and any combination thereof.

It is another object of the invention to disclose the system as defined above, wherein the system adapted to measure an acidity parameter in a food product.

It is another object of the invention to disclose the system as defined above, wherein said physical parameter is selected from the group consisting of boiling point, refractive index, viscosity, moisture content, rheologic properties, magnetic properties.

It is another object of the invention to disclose the system as defined above, wherein said electrochemical parameter is selected from conductivity, pH, oxygen content, permittivity permeability, dielectric constant and any combination thereof.

It is another object of the invention to disclose the system as defined above, wherein said chemical parameter is selected from the group consisting of chemical concentration and identity of the composition and any combination thereof.

It is another object of the invention to disclose the system as defined above, wherein said biological parameter is selected from the group consisting of bacteria, mold, fungi, alga, virus, microorganisms, eukaryotes and any combination thereof.

It is another object of the invention to disclose the system as defined above, wherein said sample is further selected from the group consisting of a solid, a sol-gel, a super-critical solution and any combination thereof.

It is another object of the invention to disclose the system as defined above, wherein said material is selected from the group consisting of water-miscible fluids, water-immiscible fluids, aggregated solutions, dispersions, emulsions, solution, slurry, polymer, solid and powder and any combination thereof.

It is another object of the invention to disclose the system as defined above, wherein said solid is selected from the group consisting of nano-particles, fine powders, flowing solids and any combination thereof.

It is another object of the invention to disclose the system as defined above, wherein said processor provides a Smith Chart of said impedance frequency variation as a function of said RF frequency such that said impedance frequency variation is function of the reactance and inductance of fluid sample.

It is still another object of the invention to disclose the system as defined above, wherein said sample comprises a fluid state.

It is another object of the invention to disclose the system as defined above, wherein said sample comprises a solid state.

BRIEF DESCRIPTION OF THE DRAWINGS

A preferred embodiment of the current invention is described hereinbelow with reference to the following drawings.

DETAILED DESCRIPTION OF PREFERRED EMBODIMENTS OF THE PRESENT INVENTION

Figure 1:
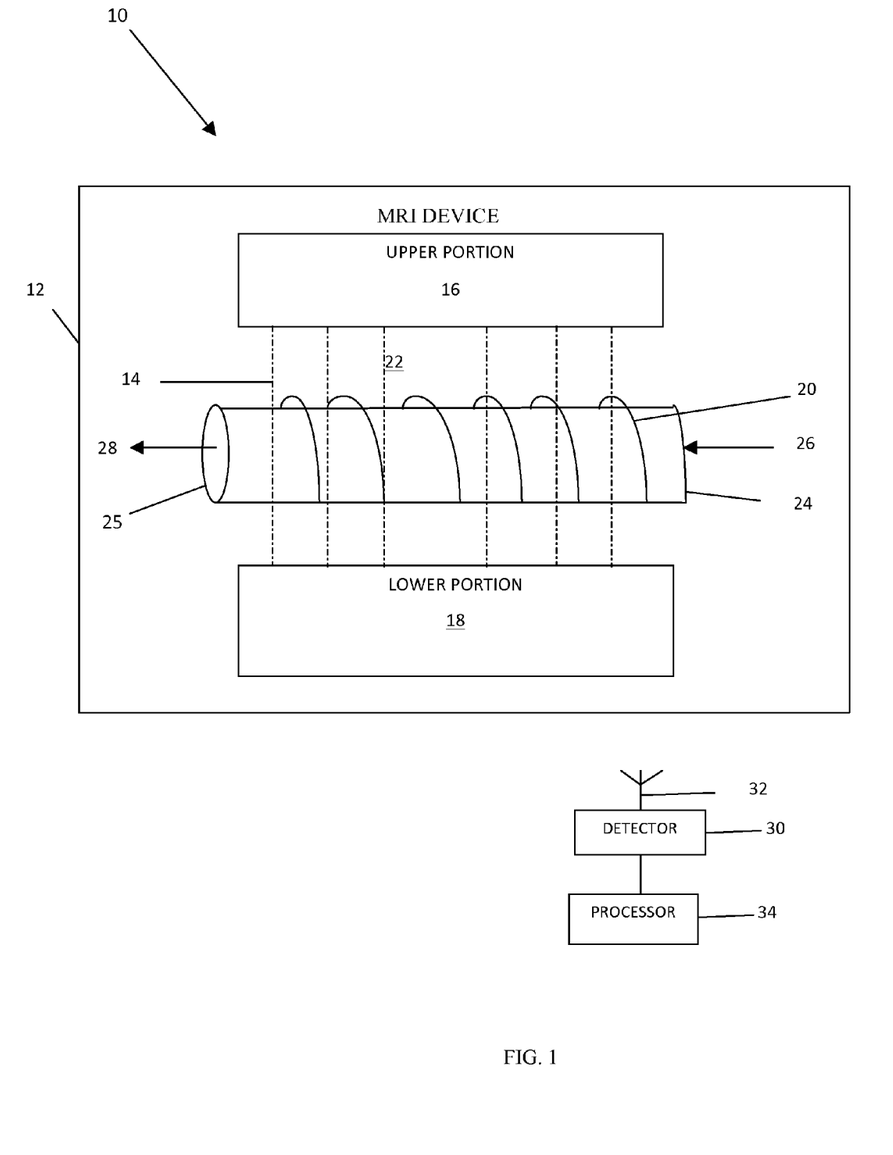
FIG. 1 shows a non-destructive on-line system for detecting a presence of a material in a sample of a substance, in accordance with a preferred embodiment of the present invention.

Reference is now made to FIG. 1, which shows a non-destructive on-line system 10 for detecting a presence of a material in a sample of a substance, in accordance with a preferred embodiment of the present invention. The non-destructive on-line system 10 includes, inter alia, an MRI device 12 for generating a magnetic field 14 between an upper portion 16 and a lower portion 18 of the MRI device 12, as is known in the art. A tunable RF coil 20 encompasses a volume of interest 22 of the MRI device 12, as is known in the art.

A flow conduit 24, which is surrounded by the tunable RF coil 20 includes an input duct 26 and an output duct 28. The sample of the substance 25 flows through the flow conduit 24 from the input duct 26 to the output duct 28.

A signal detector 30, including inter alia, an antenna 32 detects RF signals emitted by the MRI device 12 and demodulates the received signals to obtain MRI output signals, as is known in the art. Typically, the output signals are MRI voltage signals The RF frequency of the RF coil 20 is varied about an RF resonant frequency of the substance, typically, within a frequency range of ±100 MHz of the resonant frequency, such that an RF frequency spectrum is obtained. The from the signal detector 30 are frequency-dependent, V(f).

A processing unit 34 is connected to the signal detector 30 and is configured to determine an impedance frequency variation from the frequency-dependent output voltage signals, V(f), and at least one MRI device parameter. Typically, during the operation of the MRI device 12, the MRI device 12 records several operational parameters, such as the output power, (P), of the RF coil as well as the RF current, I, flowing through the RF coil 20.

Based on the MRI device operational parameters, the processing unit 34 determines a frequency-dependent impedance of the substance 30:

$$Z(f)=V(f)/I \qquad (1).$$

It is known in the art, that the impedance of a device, Z, is dependent on the reactance and inductance of the device. In particular:

$$Z(f)=R-j/2\pi fC(f)+2\pi jfL(f) \qquad (2).$$

where R is the resistance, Ω, C is the capacitive reactance, Ω, L is the inductance, H and f is the operating frequency, Hz.

Using a Smith Chart processing code, as is known in the art, the processing unit 34 determines the variation of C(f) and L(f) as a function of the RF frequency.

Figure 2:
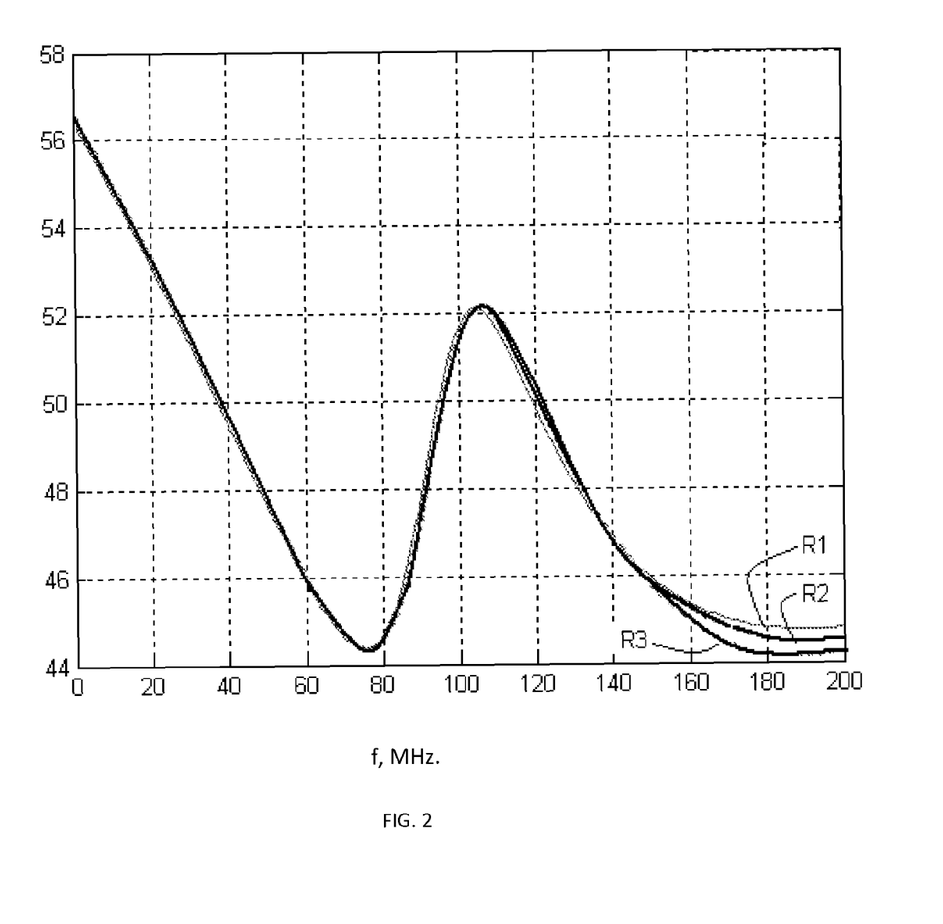
FIG. 2 shows a variation of the reactance C(f) as a function of the RF frequency for a sample of tomato puree, in accordance with a preferred embodiment of the present invention.

Reference is now made to FIG. 2, which shows a variation of the reactance C(f) as a function of the RF frequency, MHz for a sample of tomato puree, in accordance with a preferred embodiment of the present invention. The RF resonant frequency of a standard sample of tomato puree is approximately 100 MHz. FIG. 2 shows the variation of the reactances R1, R2 and R3 for the three samples of tomato puree, sample 1, sample 2 and sample 3, respectively of tomato puree as a function of the RF frequency. Each sample of tomato puree includes different amounts of water. The variation of R1 for as a function of frequency, shows the frequency-dependence reactance variation for a standard sample of tomato puree (sample 1), including one portion of water. The frequency-dependent reactance curves R2 and R3 are for tomato puree including amounts of water different than that of the standard tomato puree. Sample 2 includes a second portion of water and the sample 3 includes a third portion of water.

In FIG. 2, the curves R1, R2 and R3 represent the frequency variations of the reactances of tomato puree for the three samples, sample 1, sample 2 and sample 3, respectively. Differences in the frequency spectrum are discernible at frequencies beyond approximately 150 MHz.

Figure 3:
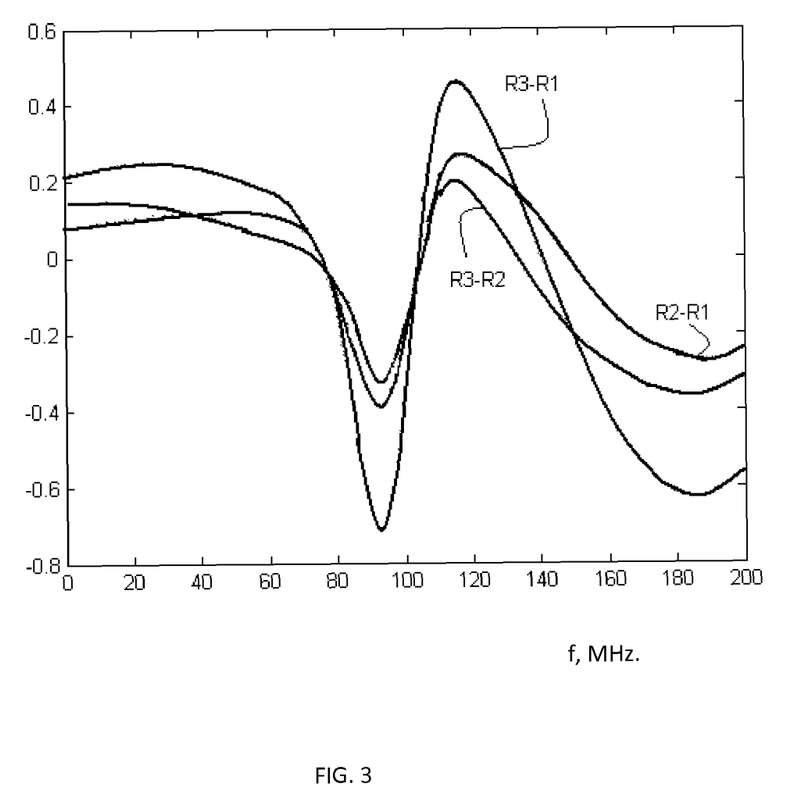
FIG. 3 shows the reactance difference curves for three samples of tomato puree, in accordance with a preferred embodiment of the present invention.

Reference is now made to FIG. 3, which shows the reactance difference curves for the three samples of tomato puree, in accordance with a preferred embodiment of the present invention. FIG. 3 shows the difference curves for the frequency-dependencies of the reactance differences (R3−R1) $\Omega$, (R2−R1) $\Omega$ and (R3−R2) $\Omega$, for sample 1, sample 2 and sample 3.

The reactance curves (R3−R1) and (R2−R1) show the reactance frequency variations relative to the reactance of the standard tomato puree, sample 1.

It is known in the art, that the MRI signal is generated by exciting the hydrogen (protons) at RF frequencies and a sample including larger quantities of water generates a larger MRI signal. Therefore, if the puree is diluted with more amounts of water than that of the standard tomato puree, the MRI signal for the diluted purees increases as a function of the amount of water dilution.

FIG. 3 shows the strength of the MRI signal is a function of the amount of water included in the sample. The curves (R3−R1) and (R2−R1) show that the tomato puree sample 2 and tomato puree sample 3, include more water than that of the standard tomato puree sample 1. Furthermore, sample 3 includes more water than sample 2.

Figure 4:
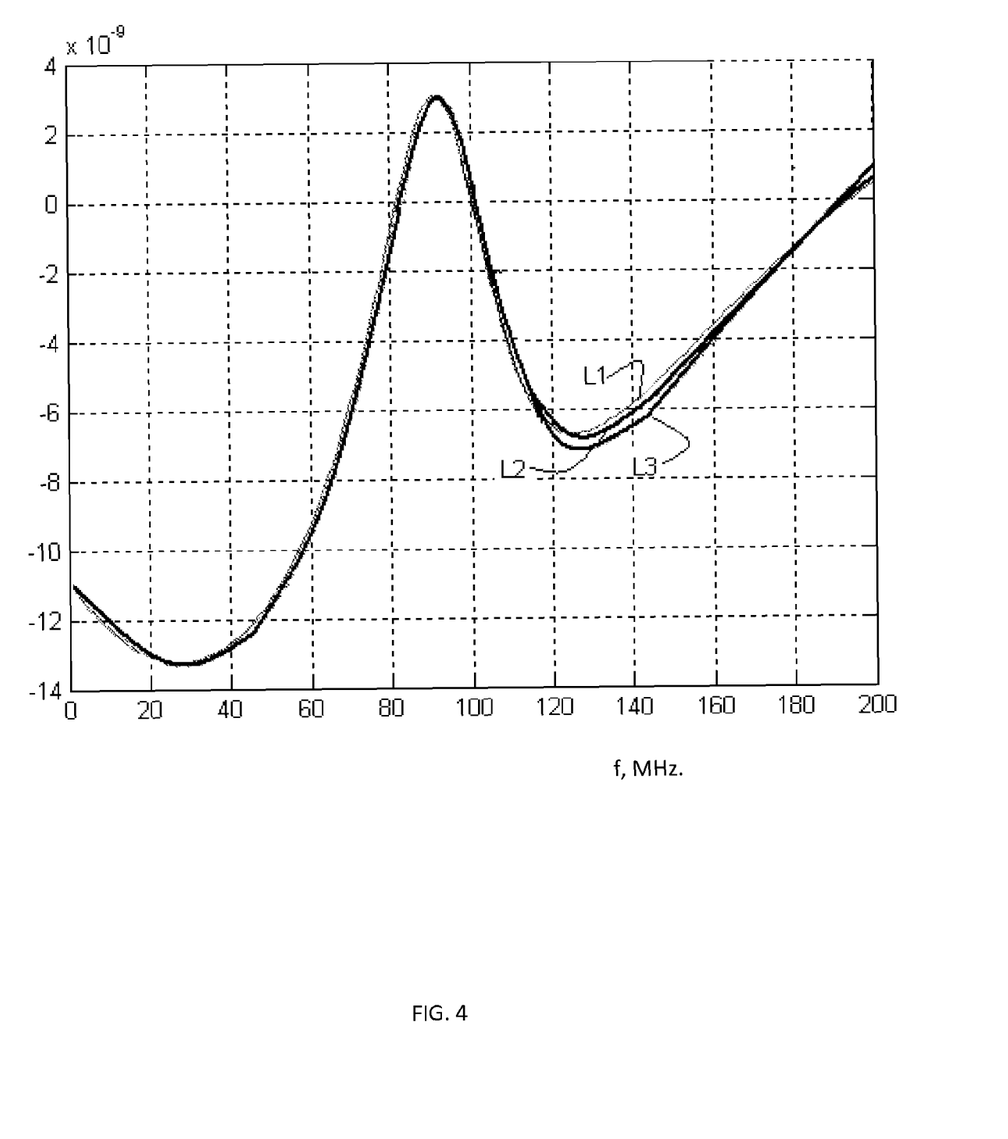
FIG. 4 shows the frequency variation of the inductance for three samples of tomato puree, in accordance with a preferred embodiment of the present invention.

Reference is now made to FIG. 4, which shows the frequency variation of the inductance L for three samples of tomato puree, in accordance with a preferred embodiment of the present invention. As shown in FIG. 4, the differences in the inductance L1, L2 and L3 are discernible in the frequency range of approximately 120-145 MHz.

FIG. 4 shows that the inductance resonance of tomato puree is at approximately 90 MHz.

Figure 5:
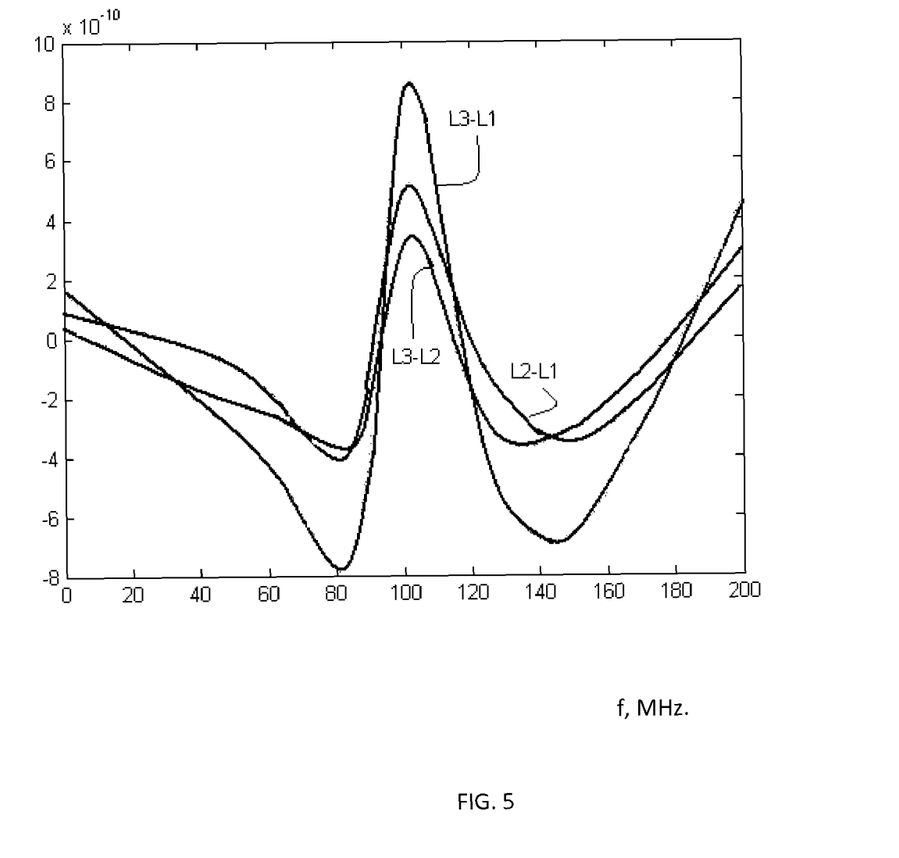
FIG. 5 shows the inductance difference curves for three samples of tomato puree, in accordance with a preferred embodiment of the present invention.

Reference is now made to FIG. 5, which shows the inductance difference curves for the three samples of tomato puree, in accordance with a preferred embodiment of the present invention. FIG. 5 shows the difference curves for the frequency-dependencies of the reactance differences (L3−L1) H, (L2−L1) H and (L3−L2) H, for sample 1, sample 2 and sample 3.

The inductance difference curves (L3−L1) and (L2−L1) show the reactance frequency variations relative to the reactance of the standard tomato puree, sample 1 with inductance the frequency-dependency L1.

FIG. 5 shows the strength of the MRI signal is a function of the amount of water included in the sample. The difference curves (L3−L1) and (L2−L1) show that the tomato puree sample 2 and tomato puree sample 3, include more water than that of the standard tomato puree sample 1. Furthermore, sample 3 includes more water than sample 2.

Thus, using the system shown in FIG. 1 it is possible to test if a sample of a food product fulfills food standard criteria regarding the amounts of water contained therein. It is appreciated that the system of FIG. 1 is also available for determining additional characteristics of the substance, such as physical, chemical, electrochemical and biological parameters and characteristics of the sample of the substance.

Figure 6:
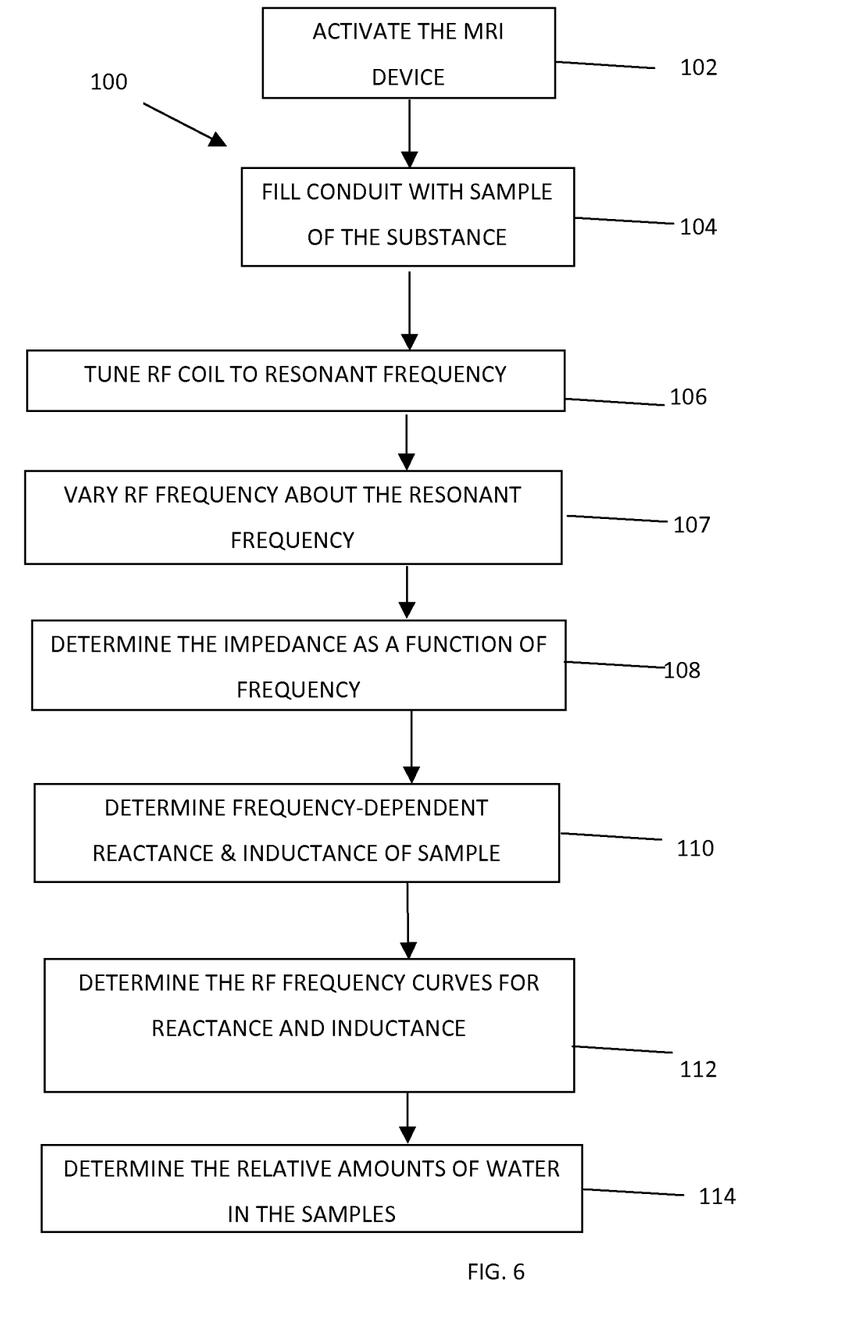
FIG. 6 shows a flow chart for a non-destructive on-line method for detecting a material in a sample of a substance, in accordance with a preferred embodiment of the present invention.

Reference is now made to FIG. 6, which shows a flow chart 100 for a non-destructive on-line method for detecting a material in a sample of a substance, in accordance with a preferred embodiment of the present invention. In step 102, the MRI device 12 is activated and the flow conduit 24 is filled with substance 25 (step 104).

In step 106, the RF coil 20 is tuned to the resonant frequency of the substance and the MRI signal voltage is recorded. In step 107, the RF frequency of the RF coil 20 is varied within a frequency range of ±100 MHz about the resonant frequency and the MRI voltage signal value is recorded at each frequency step.

In step 108, an MRI operational parameter, such as the RF coil current, is recorded from the MRI device's operating parameters and combining this RF current value with the MRI output signal voltage, a variation of the impedance of the sample as a function of the RF frequency is determined.

In step 110, in accordance with equation (2) and the Smith Curve code, as is known in the art, the RF frequency variation of the sample's reactance and inductance are determined.

In step 112, the RF frequency difference curves of the sample's reactance and inductance are recorded and in step 114, the amount of water dilution of the sample is determined.

Figure 7:
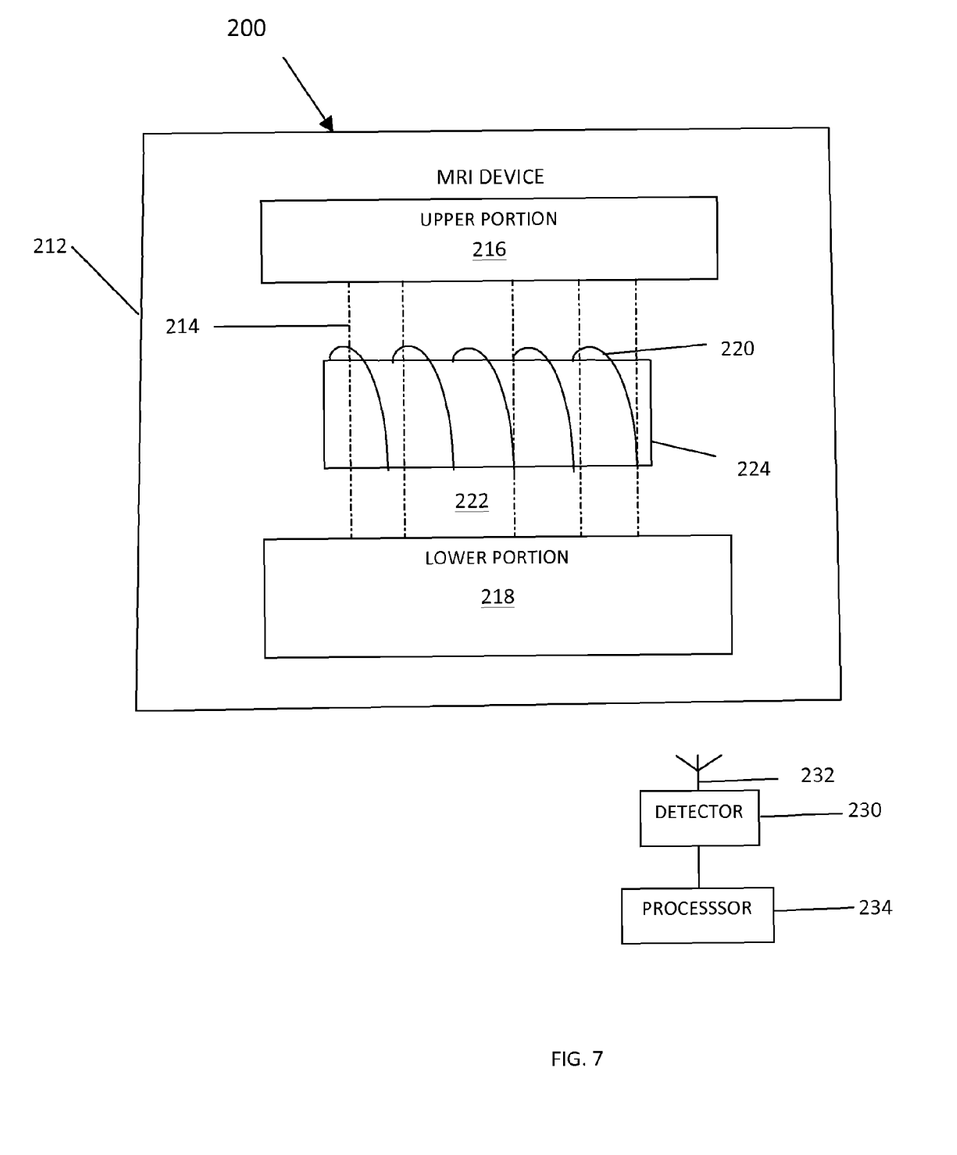
FIG. 7 shows a non-destructive on-line system for detecting a presence of a material in a substance, in accordance with another preferred embodiment of the present invention.

Reference is now made to FIG. 7, which shows a non-destructive on-line system 200 for detecting a presence of a material in a substance, in accordance with another preferred embodiment of the present invention. The non-destructive on-line system 200 includes, inter alia, an MRI device 212 for generating a magnetic field 214 between an upper portion 216 and a lower portion 218 of the MRI device 212, as is known in the art. An tunable RF coil 220 is located in a volume of interest 222 of the MRI device 212, as is known in the art.

A container 224 is encompassed by the tunable RF coil 220 and includes a sample of the substance for testing the amount of water dilution.

A signal detector 230, including inter alia, an antenna 232 detects MRI signals emitted by the MRI device 212 and demodulates the received signals to obtain MRI signals, as is known in the art. Typically, the output signals are MRI voltage signals The RF frequency of the RF coil 220 is varied about an RF resonant frequency of the substance, typically, within a frequency range of ±100 MHz of the resonant frequency, such that an RF frequency spectrum is obtained. The variation of the RF frequency results in the output voltage signals from the signal detector 230 are frequency-dependent.

A processing unit 234 is connected to the signal detector 232 and is configured to determine an impedance frequency variation from the frequency-dependent output voltage signals, V(f), and at least one MRI device parameter. Typically, during the operation of the MRI device 212, the MRI device 212 records several operational parameters, such as the output power, (P), of the RF coil as well as the RF current flowing through the coil, I.

Based on these parameters, the processing unit 234 determines a frequency-dependent impedance of the sample of substance 230 and the and the frequency-dependent reactances and inductances, using a Smith Chart processing code, as is known in the art and as described hereinabove. The processing unit 234 determines the variation of C(f) and L(f) as a function of the RF frequency.

EXAMPLES

Below are given various examples which demonstrate the use of the present invention for on-line nondestructive testing. The examples describe the manner and process of the present invention and set forth the best mode contemplated by the inventors for carrying out the invention. These examples are not to be construed as limiting the invention.

Example 1

A water salinity check can be used for homeland security in the event of a spilling a poison, contaminant or chemical in a water reservoir. Although many of the existing detection single devices can detect contaminants at very low concentrations, these devices are often specific to a contaminant or a group of contaminants. Since the physical and chemical properties of contaminants can vary greatly and instruments which check for the existence of a specific contaminant is not useful if the of little use because that contaminant may not be the one used. Most of the biological monitors, such as the use of algae, had limited distribution system. Monitors that use fish or mussels can detect cyanide and chlorinated pesticides, but not at the desired detection limit.

Using the present invention, water from a water-well is pumped through the fluid conduit of the present invention and MRI measurements of the water flow are performed. The MRI signals from the water flow are recorded. The RF frequency of the RF coil is adjusted to the resonance frequency of water and the frequency of the RF coil is adjusted about the resonance frequency. The frequency-dependent reactance and inductance plots for the water flow are determined from a Smith Curve code and the quality of the water flow is monitored. The variation of the reactance and inductance plots from a standard plots enables detection of the water composition change. An alert is activated if the system detects a predetermined significant change.

Example 2

The current invention is operated in a ketchup production line. The MRI device is calibrated to the standard resonance frequency of a tomato ketchup. The MRI signals from the ketchup flow through the flow conduit are recorded. The RF frequency of the RF coil is adjusted to the resonance frequency of the tomato ketchup and the frequency of the RF coil is adjusted about the resonance frequency. The frequency-dependent reactance and inductance plots for the ketchup flow are monitored continuously. On-line information, such as water quantity or water activity, Aw, are also available, enabling either an automatic or manual response to diversions therefrom. Typically, an alert is activated if the system detects a predetermined change, such as 0.5%, in the reactance and/or inductance resonant values. Thus, the amount of water may be increased or decreased to the ketchup according to the customer requirements and preferences.

Example 3

The current invention is operated in an apple puree production line. The MRI device is calibrated to the standard resonance frequency of the apple puree. The MRI signals from the apple puree flow through the flow conduit are recorded. The RF frequency of the RF coil is adjusted to the resonance frequency of the apple puree and the frequency of the RF coil is adjusted about the resonance frequency. The frequency-dependent reactance and inductance plots for the apple puree flow are monitored continuously. On-line information, such as water quantity or water activity, Aw, are also available, enabling either an automatic or manual response to diversions therefrom. Typically, an alert is activated if the system detects a predetermined change, such as 0.5%, in the reactance and/or inductance resonant values. Thus, the amount of water may be increased or decreased to the apple puree according to the customer requirements and preferences.

Example 4

In the chemical industry it is desired to minimize human exposure to chemicals, such as dangerous chemicals and explosives, for safety reasons and to avoid human error. Using the present invention, it is possible to determine changes in concentration of particular chemicals, such as hydrogen peroxide concentration, in the fluid conduit and determine the diversions from the RF resonant frequency of different chemicals. The current invention performs a correlation, such as a linear correlation, between the reactance and inductance RF frequency resonant values and the determines a percentage of a particular chemical component, for example, hydrogen peroxide, glycol in the process chemical or slurry in the fluid conduit.

Example 5

Using the present invention to provide an automated and non-invasive on-line monitoring of chemical reactions, such as $NaOH+Cl_2 \rightarrow NaOCl+HCl$. The frequency-dependency of the reactances and inductances are determined about the resonant frequency are recorded.

Example 6

The system also provides an automated and non-invasive monitoring on grain stream. The information of the grain monitoring is used to establish the quality characteristics and the value of the grain. The monitoring is also necessary for proper grain storage management. Information from the grain, such as grain moisture content and the amount of foreign material, can be used to determine appropriate action to maintain the quality of the stored product. The distribution of constituents is generally not uniform throughout the load; the constituents of the grain mass stratify and segregate. This causes variations in the physical characteristics within the load. The air space between the grain constituents cause leaps in the measurement. The method of monitoring is therefore extremely important to ensure that the grain stream is truly representative of the whole grain mass. The frequency per unit volume of grain is measured. A smith chart is of measured and the measurement on the resonant frequency is recorded. The information about the obtained grain moisture is the average moisture of the whole grain mass.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A non-destructive on-line system for detecting a presence of a material a substance comprising:
   an MRI device comprising a tunable RF coil and a signal detector, said signal detector is configured for detecting frequency-dependent output signals as a function of a frequency variation of the RF tunable coil within a frequency range of an RF resonant frequency of a standard sample of said substance;
   a flow conduit encompassed by said tunable RF coil and having an input duct and an output duct to allow a flow of said substance therethrough; and
   a processing unit,
   wherein said processing unit is configured to:
      receive said frequency-dependent output signals from said detector;
      determine an impedance frequency variation from said frequency-dependent output signals and at least one operational parameter of the MRI device;
      determine RF frequency variation of inductance and RF variation of reactance from said impedance frequency variation; and
      compare at least one of the RF frequency variation of the inductance and the RF frequency variation of the electrical reactance with an RF frequency variation of a corresponding inductance or reactance of said standard sample of said substance such that said comparison determines said material content of said substance.

2. The non-destructive on-line method according to claim 1, wherein said frequency range is approximately from said resonant frequency minus 100 MHz to said resonant frequency plus 100 MHz.

3. The non-destructive on-line method according to claim 1, wherein said material comprises water.

4. The non-destructive on-line system according to claim 1, wherein said output signal comprises either a voltage signal or an RF voltage signal.

5. The non-destructive on-line system according to claim 1, wherein said processing unit is further configured to optimize a production process of said sample.

6. The system according to claim 1, adapted to measure and control the sample undergoing a modification said modification is selected from the group consisting of a physical modification, biological modification, chemical modification and any combination thereof.

7. The non-destructive on-line system according to claim 1, wherein said substance is selected from the group consisting of tomato puree, tomato ketchup, tomato paste, tomato sauce, tomato beverage, tomato soup, tomato concentrate, apple puree, apple paste, apple sauce, apple beverage, apple concentrate, potato puree, potato paste, potato sauce, potato beverage, potato concentrate.

8. The non-destructive on-line system according to claim 1, adapted to measure and to control water pollution by at least one contaminant said at least one contaminant is selected from organic contaminants, inorganic contaminants and any combination thereof.

9. The non-destructive on-line system according to claim 1, adapted to measure an acidity parameter in a food product.

10. The non-destructive on-line system according to claim 1, wherein said substance is selected from the group consisting of water-miscible fluids, water-immiscible fluids, aggregated solutions, dispersions, emulsions, solution, slurry, polymer, solid and powder and any combination thereof.

11. The non-destructive on-line according to claim 1, wherein said processor provides a Smith Chart of said impedance frequency variation as a function of said RF frequency and wherein said RF frequency variation of inductance and said RF variation of reactance are determined by use of said Smith Chart.

12. The non-destructive on-line system according to claim 1, wherein said sample comprises either a fluid state or a solid state.

13. A non-destructive on-line method for detecting a material in a sample of a substance comprising:
   providing an MRI device comprising a tunable RF coil;
   providing a flow conduit encompassed by the tunable RF coil of said MRI device;
   providing a flow of said sample through said flow conduit;
   detecting frequency-dependent output signals from said MRI device as a function of a frequency variation of the RF tunable coil within a frequency range of an RF resonant frequency of a standard sample of said substance, and
   determining an impedance frequency variation from said frequency-dependent output signals and at least one predetermined MRI operational parameter;
   determining an RF frequency variation of inductance and/or reactance of said substance from said impedance frequency variation;
   comparing said RF frequency variation of said inductance and/or reactance of said substance with an RF frequency variation of a corresponding inductance and/or reactance of the standard sample of said substance,
   wherein said comparison determines said material content of said sample.

14. A non-destructive on-line system for detecting a presence of a material in a sample of a substance comprising:
   an MRI device comprising a tunable RF coil and a signal detector, said signal detector is configured for detecting frequency-dependent output signals as a function of a frequency variation of the RF tunable coil within a frequency range of an RF resonant frequency of a standard sample of said substance;
   a container encompassed by said tunable RF coil containing said sample of a substance; and
   a processing unit,
   wherein said processing unit is configured to:
      receive said frequency-dependent output signals from said detector;
      determine an impedance frequency variation from said frequency-dependent output signals and at least one operational parameter of the MRI device;
      determine RF frequency variation of inductance and RF variation of reactance from said impedance frequency variation; and
      compare at least one of the RF frequency variation of the inductance and the RF frequency variation of the electrical reactance with an RF frequency variation of a corresponding inductance or reactance of said standard sample of said substance such that said comparison determines said material content of said sample of a substance.

* * * * *